United States Patent
Kline (10) Patent No.: US 8,491,494 B2
(45) Date of Patent: Jul. 23, 2013

(54) DISPOSABLE HAND-HELD DEVICE FOR COLLECTION OF EXHALED BREATH CONDENSATE

(75) Inventor: Jeffrey A. Kline, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 1635 days.

(21) Appl. No.: 11/799,176

(22) Filed: May 1, 2007

(65) Prior Publication Data

US 2007/0203424 A1  Aug. 30, 2007

Related U.S. Application Data

(62) Division of application No. 10/742,721, filed on Dec. 19, 2003, now abandoned.

(60) Provisional application No. 60/434,916, filed on Dec. 20, 2002, provisional application No. 60/447,581, filed on Feb. 14, 2003.

(51) Int. Cl.
*A61B 5/08* (2006.01)

(52) U.S. Cl.
USPC .......................................... 600/543; 600/529

(58) Field of Classification Search
USPC .......................................................... 600/543
See application file for complete search history.

(56) References Cited

U.S. PATENT DOCUMENTS

| | | | |
|---|---|---|---|
| 3,000,379 A | 9/1961 | Viers | 121/191 |
| 3,420,224 A | 1/1969 | Farr | 128/2.07 |
| 3,509,771 A | 5/1970 | Moberg et al. | |
| 3,613,665 A | 10/1971 | Gorsuch | 128/2 R |
| 3,622,278 A | 11/1971 | Elzinga et al. | 23/232 R |
| 3,799,149 A | 3/1974 | Rummel et al. | |
| 3,830,630 A | 8/1974 | Kiefer et al. | 23/232 E |
| 3,891,508 A | 6/1975 | Merrick | |

(Continued)

FOREIGN PATENT DOCUMENTS

| | | |
|---|---|---|
| EP | 0 759 169 B1 | 1/1998 |
| EP | 0919810 B1 | 1/2002 |

(Continued)

OTHER PUBLICATIONS

International Search Report, PCT/US04/04321, International Filing Date Feb. 13, 2004.

(Continued)

*Primary Examiner* — Patricia Mallari
*Assistant Examiner* — Michael D'Angelo
(74) *Attorney, Agent, or Firm* — K&L Gates LLP (57) ABSTRACT

A breath condensate collection apparatus comprising a central chamber, a breath input assembly, a plunger assembly and a breath condensate collection port. The central chamber has inner and outer side walls with a coolant material sealed in between. The breath input assembly is disposed on the side of the central chamber in fluid communication with the chamber interior. The plunger assembly has a piston, slidably disposed in the chamber, and a handle extending from a first end of the chamber. The collection port is disposed at the second end of the central chamber in fluid communication with the interior of the chamber. Obstructive structures may be arranged in the chamber interior for increasing the surface area on which condensate may form. The apparatus may also include an outlet assembly that may be removed and replaced with a sampling well into which the condensate may be washed with a buffer solution.

3 Claims, 9 Drawing Sheets

U.S. PATENT DOCUMENTS

| | | | |
|---|---|---|---|
| 4,248,245 A | 2/1981 | Kempin | 128/719 |
| 4,259,951 A | 4/1981 | Chernack et al. | 128/200.14 |
| 4,322,217 A | 3/1982 | Dikeman | 23/230 B |
| 4,349,626 A | 9/1982 | Labows et al. | 435/38 |
| 4,370,413 A | 1/1983 | Neeman et al. | 435/39 |
| 4,438,209 A | 3/1984 | Mosier | 436/542 |
| 4,491,660 A | 1/1985 | Gendrich et al. | 536/32 |
| 4,510,241 A | 4/1985 | Mills | 435/23 |
| 4,717,658 A | 1/1988 | Michaels | |
| 4,784,486 A | 11/1988 | Van Wagenen et al. | |
| 4,818,489 A | 4/1989 | Gönner et al. | 422/84 |
| 4,870,158 A | 9/1989 | Karol et al. | |
| 5,042,501 A | 8/1991 | Kenny et al. | 128/719 |
| 5,186,242 A | 2/1993 | Adachi et al. | |
| 5,198,339 A | 3/1993 | Hansen et al. | |
| 5,285,794 A * | 2/1994 | Lynch | 600/532 |
| 5,310,657 A | 5/1994 | Berzofsky | 435/34 |
| 5,327,901 A | 7/1994 | Delente | 128/730 |
| 5,356,778 A | 10/1994 | Hansen et al. | 435/7.2 |
| 5,376,555 A | 12/1994 | Forrester et al. | 436/132 |
| 5,380,295 A * | 1/1995 | Vacca | 604/187 |
| 5,383,469 A | 1/1995 | Vreman et al. | 128/719 |
| 5,465,728 A | 11/1995 | Phillips | 128/730 |
| 5,479,815 A | 1/1996 | White et al. | |
| 5,487,380 A | 1/1996 | Grabenkort | 128/204.15 |
| 5,501,212 A | 3/1996 | Psaros | 128/205.12 |
| 5,541,057 A | 7/1996 | Bogart et al. | 435/5 |
| 5,558,087 A | 9/1996 | Psaros et al. | 128/205.12 |
| 5,625,189 A | 4/1997 | McCaul et al. | |
| 5,634,517 A | 6/1997 | Linden et al. | 165/111 |
| 5,655,526 A | 8/1997 | Gibertoni | 128/205.27 |
| 5,702,882 A | 12/1997 | Tamura et al. | 435/4 |
| 5,759,858 A | 6/1998 | Nieuwenhuizen | 436/16 |
| 5,787,885 A | 8/1998 | Lemelson | 128/632 |
| 5,795,787 A | 8/1998 | Silkoff et al. | 436/116 |
| 5,826,575 A | 10/1998 | Lall | 128/205.12 |
| 5,876,947 A | 3/1999 | Kudryk et al. | 435/7.1 |
| 5,938,637 A | 8/1999 | Austin et al. | 604/72 |
| 5,998,389 A | 12/1999 | Loverock | 514/54 |
| 6,010,459 A | 1/2000 | Silkoff et al. | 600/532 |
| 6,033,368 A | 3/2000 | Gaston, IV et al. | 600/532 |
| 6,106,783 A | 8/2000 | Gamble | |
| 6,132,610 A | 10/2000 | Hirai et al. | 210/264 |
| 6,139,506 A | 10/2000 | Heinonen | |
| 6,148,657 A | 11/2000 | Satoh et al. | 73/23.35 |
| 6,149,603 A | 11/2000 | Parker | 600/532 |
| 6,186,958 B1 | 2/2001 | Katzman et al. | 600/532 |
| 6,221,026 B1 | 4/2001 | Phillips | 600/532 |
| 6,244,096 B1 | 6/2001 | Lewis et al. | |
| 6,283,122 B1 | 9/2001 | Adahan | 128/205.24 |
| 6,312,390 B1 | 11/2001 | Phillips | 600/532 |
| 6,341,520 B1 | 1/2002 | Satoh et al. | 73/23.35 |
| 6,363,772 B1 | 4/2002 | Berry | 73/24.02 |
| 6,384,188 B1 | 5/2002 | Hoess et al. | 530/326 |
| 6,419,634 B1 | 7/2002 | Gaston, IV et al. | 600/532 |
| 6,461,306 B1 * | 10/2002 | Hanson et al. | 600/532 |
| 6,491,643 B2 | 12/2002 | Katzman et al. | 600/532 |
| 6,582,376 B2 | 6/2003 | Baghdassarian | 600/543 |
| 6,585,661 B1 * | 7/2003 | Hunt et al. | 600/532 |
| 6,612,306 B1 | 9/2003 | Mault | 128/204.22 |
| 6,645,724 B1 | 11/2003 | Ding et al. | 437/7.1 |
| 6,656,127 B1 | 12/2003 | Ben-Oren et al. | 600/532 |
| 6,660,852 B1 | 12/2003 | Keshi et al. | |
| 6,726,637 B2 | 4/2004 | Phillips | 600/543 |
| 6,824,520 B2 | 11/2004 | Orr et al. | 600/529 |
| 7,066,892 B2 | 6/2006 | Kline | |
| 7,118,537 B2 | 10/2006 | Baddour | 600/543 |
| 7,300,408 B2 | 11/2007 | Hancock et al. | |
| 7,547,285 B2 | 6/2009 | Kline | 600/532 |
| 7,828,741 B2 | 11/2010 | Kline et al. | 600/532 |
| 2001/0021815 A1 | 9/2001 | Katzman et al. | 600/532 |
| 2003/0045807 A1 | 3/2003 | Daniels, II et al. | |
| 2003/0050567 A1 | 3/2003 | Baghdassarian | 600/532 |
| 2003/0109794 A1 | 6/2003 | Phillips | |
| 2003/0109795 A1 | 6/2003 | Webber | |
| 2003/0208132 A1 | 11/2003 | Baddour | 600/532 |
| 2004/0138577 A1 | 7/2004 | Kline | 600/543 |
| 2004/0162500 A1 | 8/2004 | Kline | 600/532 |
| 2004/0234971 A1 | 11/2004 | Jackman | 435/6 |
| 2005/0196868 A1 | 9/2005 | Kline | 436/66 |
| 2005/0208614 A1 | 9/2005 | Kline | 435/34 |
| 2007/0073183 A1 | 3/2007 | Kline | 600/532 |
| 2007/0100250 A1 | 5/2007 | Kline | 600/532 |

FOREIGN PATENT DOCUMENTS

| | | | |
|---|---|---|---|
| WO | WO 01/84112 | * | 11/2001 |
| WO | WO 01/84112 A1 | | 11/2001 |
| WO | WO 02/082977 A2 | | 10/2002 |
| WO | PCT/US03/41209 | | 12/2003 |
| WO | PCT/US05/006908 | | 3/2005 |
| WO | WO 2006/007180 A2 | | 1/2006 |
| WO | PCT/US06/19911 | | 5/2006 |

OTHER PUBLICATIONS

International Search Report, PCT/US05/18232, International Filing Date May 24, 2005.

*National Hospital Ambulatory Medical Care Survey: 2002 Emergency Department Summary*, Linda F. McCaig et al., Division of Health Care Statistics, U.S. Department of Health and Human Services, No. 340, Mar. 18, 2004, pp. 1-35.

*A Rapid Qualitative Assay to Detect Circulating Endotoxin Can Predict the Development of Multiorgan Dysfunction*, M.H. Kollef et al, CHEST, vol. 112,173-180, © 1997 by American College of Chest Physicians, http://www.chestjournal.org/cgi/content/abstract/112/1/173, May 21, 2004, 1 page.

*Untersuchungen zur Anwendbarkeit der Atemkondensatgewinnung beim Pferd und ihre Potentiellen Einsatzmöglichkeiten in der Lungendiagnostik*, Sandra Schack, Abstract, http://bibd.uni-giessen.de/ghtm/2002/uni/d020068b.htm, Nov. 19, 2002, 1 page.

*Total Nitrite/Nitrate in Expired Breath Condensate of Patients With Asthma*, K. Ganas et al., PNEUMON, http://www.mednet.gr/pneumon/1403-6e.htm, Nov. 19, 2002, 1 page.

U.S. Appl. No. 10/884,179, filed Jul. 4, 2004, Kline.

*Breath Condensate: Rich Source of Exhaled Markers and Mediators. Methodological Issues and Standardisation of Measurements*, Kharitonov et al., National Heart and Lung Institute, Imperial College, Dovehouse Street, London SW3 6LY, UK, www.filt.de/Hauptmenue/Aktuelles_Current_Affairs/Page10464/Breath/_Condensate, Nov. 19, 2002, 2 pages.

*Mycobacterium tuberculosis Gene-Amplification in Breath Condensate of Patients with Lung Tuberculosis*, J. Schreiber et al., European Journal of Medical Research, Jun. 28, 2002, pp. 290-291.

*Expired Hydrogen Peroxide in Breath Condensate of Cystic Fibrosis Patients*, L.P. Ho et al., Abstract, Eur Respir J 1999; 13:103-106, http://www.personal.u-net.com/, Nov. 19, 2002.

*Meeting Report—World Congress on Lung Health and 10$^{th}$ ERS Annual Congress* Aug. 30-Sep. 3, 2000, Florence, Italy, Pieter S. Hiemstra, Respir Res 2000, 1:178-179, http://respiratory-research.com/content/1/3/178.

*Breath Condensate*, info Special Edition, 1$^{st}$ Edition, Apr. 2001, JAEGER a subsidiary of VIASYS Healthcare, Hoechberg, Germany, pp. 1-28.

*Diagnosis of Gram Negative, Ventilator Associated Pneumonia by Assaying Endotoxin in Bronchial Lavage Fluid*, P.G. Flanagan et al., J. Clin Pathol 2001:54:107-110, Mar. 16, 2005; www.jcp.bmjjournals.com.

*Rapid Diagnosis of Gram Negative Pneumonia by Assay of Endotoxin in Bronchoalveolar Lavage Fluid*, Jerome Pugin et al. Thorax 1992: 47:547-549.

*Pseudomonas aeruginosa and Burkholderia cepacia Cannot Be Detected by PCR in the Breath Condensate of Patients With Cystic Fibrosis*, Vogelberg, C., et al. ; Pediatric Pulmonology 36:348-352 (2003).

Sergei A. Kharitonov and Peter J. Barnes, "Exhaled Markers of Pulmonary Disease", *American Journal of Respiratory and Critical Care Medicine*, vol. 163, pp. 1693-1722, 2001.

George Nakos, Eirene I. Kitsiouli and Marilena E. Lekka, "Bronchoalveolar Lavage Alterations in Pulmonary Embolism," *American Journal of Respiratory and Critical Care Medicine*, vol. 158, p. 1504, 1998.

Matthias Griese, Jochen Noss, Christina von Bredow, "Protein Pattern of Exhaled Breath Condensate and Saliva", *Proteomics* 2002, 2, pp. 690-696.

Zlotnick and Yoshie, "Chemokines: A New Classification System and Their Role in Immunity," *Immunity*, 2000, 12:121-127.

Kimura et al. "Alleviation of Monocrotaline-Induced Pulmonary Hypertension by Antibodies to Monocyte Chemotactic and Activating Factor/Monocye Chemoattractant Protein-1," *Lab Invest* 1998 78:571-81.

Supplementary European Search Report—EP 03 81 4375.

Luna et al. "Impact of BAL Data on the Therapy and Outcome of Ventilator-Associated Pneumonia" Chest 1997; 111; 676-685. accessed at http://chestjournal.org/cgi/content/abstract/111/3/676.

Moloney et al. "Exhaled Breath Condensate Detects Markers of Pulmonary Inflammation after Cardiothoracic Surgery". American Journal of Respiratory and Critical Care Medicine, vol. 169, pp. 64-69, 2004.

Lindsay et al. "Single-Step, Chromogenic Limulus Amebocyet Lysate Assay for Endotoxin". Journal of Clinical Microbiology, May 1989, pp. 947-951.

F. Nyeri, et al., "Exhaled breath condensate and serum levels of hepatocyte growth factor in pneumonia", Respiratory Medicine, vol. 96 (Dec. 10, 2002) p. 115-119, Bailliere Tindall, London, GB.

\* cited by examiner

DISPOSABLE HAND-HELD DEVICE FOR COLLECTION OF EXHALED BREATH CONDENSATE

CROSS-REFERENCE TO RELATED APPLICATIONS

This application is a divisional of and thus is entitled to the benefit of, and claims priority to, provisional U.S. Patent Application Ser. No. 60/434,916 filed Dec. 20, 2002 and entitled "DISPOSABLE HAND-HELD DEVICE FOR COLLECTION OF EXHALED BREATH CONDENSATE FOR ASSAY OF BIOMARKERS FOR THE DETECTION AND PROGNOSIS OF LUNG ISCHEMIA," provisional U.S. Patent Application Ser. No. 60/447,581 filed Feb. 14, 2003 and entitled "DEVICE AND METHOD FOR COLLECTION OF EXHALED ALVEOLAR BREATH CONDENSATE," and U.S. patent application Ser. No. 10/742,721 filed Dec. 19, 2003 and entitled "DISPOSABLE HAND-HELD DEVICE FOR COLLECTION OF EXHALED BREATH CONDENSATE," the entirety of each of which is incorporated herein by reference.

BACKGROUND OF THE PRESENT INVENTION

1. Field of the Present Invention

The present invention relates to the collection of breath condensate medical testing and diagnosis, and, in particular, to a double-walled chamber having a coolant material embedded between the inner and outer walls, a side-mounted breath input assembly, an outlet from which condensate may be collected, and a plunger for expressing the condensate through the outlet. The collected sample may then be tested for biomarkers indicating the presence and severity of lung ischemia and associated pulmonary vasoconstriction.

2. Background

Approximately 6% of exhaled breath is water vapor and water droplets. One source of water in breath is from the fluids that line the alveoli of the lung. In other words, the water vapor exhaled from the breath equilibrates with fluid in the bronchi and alveoli, and therefore breath condensate collection provides a noninvasive means of sampling these fluids.

Exhaled breath condensate contains water soluble and water insoluble molecules, including dissolved gases, organic solutes, ions and proteins. Breath condensate samples from patients with certain diseases have been shown to contain elevated content of inflammatory molecules. For example, previous work has demonstrated that smoking, asthma and cystic fibrosis increase the presence of prostaglandin derivatives, thromboxane, leukotrienes and cytokines. (S A Kharitonov and P J Barnes, Exhaled markers of pulmonary disease, *Am J Respir Crit Care Med* 163:1693-1722, 2001.) Until recently, though, little work has been done to identify biomarkers in exhaled breath water vapor that may be able to assist in determining the presence and severity of lung ischemia.

However, recent research indicates that it may be possible to detect lung ischemia by performing a battery of tests on relatively small breath condensate samples. A proposed battery of tests for lung ischemia may include fibrinopeptides, thromboxane B2, platelet activating factor, leukotrienes C, D and E, carbon monoxide-to-nitric oxide ratio and chemokine and other proteins. Measurement of fibrinopeptides in breath condensate is believed to have the potential to allow more localized measurement of the presence of clot in the lung vasulature. It is publicly known that thrombin cleaves fibrinogen A peptide from fibrinogen as a prerequisite to fibrin gelation. Owing to its small size, it is hypothesized that fibrinopeptides will traverse the alveolar membrane, and equilibrate in alveolar fluid, and thus will be found in exhaled condensate.

It is also believed that pulmonary vascular constriction may be detected by measuring $PGF_{2\alpha}$, thromboxane $B_2$, PAF, leukotrienes C, D, and E, and the ratio of CO to NO in condensate, thus providing a basis for initiating pulmonary vasodilator therapy or COX1,2 inhibition. Our laboratory has used an experimental pulmonary vascular occlusion (PVO), induced by venous infusion of polystyrene microspheres in a rat, to determine three major findings related to breath condensate analysis. We and others have found increased content of $PGF_{2\alpha}$, thromboxane $B_2$, platelet activating factor (PAF) and vasoconstrictive leukotrienes C, D, and E in the lung washings in our rat model. (Nakos, Am J Resp Crit Care Med 1998, 158:1504) The magnitude of the concentration of these vasoconstrictive agents correlated with the severity of hypoxemia and pulmonary hypertension. We also have found extremely elevated expression of the gene encoding heme oxygenase-1 but the nearly complete absence of expression of the gene encoding for the inducible enzyme, nitric oxide synthase. Heme oxygenase produces carbon monoxide (CO) from heme substrate whereas nitric oxide synthase produces nitric oxide (NO). Both are vasodilator substances. In rats subjected to PVO, we have also found early increases in lung gene expression of cytokine induced neutrophil attractant 1 and 2 (CINC 1 & 2), and monocyte/macrophage chemoattractant protein (MCP) 1 and 2, and monocyte/macrophage inflammatory proteins (MIP) 1 $\alpha$ and 1 $\beta$ with concomitant increases in each protein in the washings from the lung airways and alveoli obtained as soon as 2 hours after induction of PE, and lasting up to 18 hours after PE induction. The chemoattractant molecules can cause the migration of leukocytes into the affected area, and through this mechanism, can potentiate injury during therapeutic reperfusion.

Further, the presence of certain chemokines in exhaled condensate is believed to predispose reperfusion injury. The chemokines discovered in rats included CINC 1, CINC 2, MIP 1$\alpha$, MIP 1$\beta$, and MCP 1 and 2. The human homologues that will be tested in our device will include CXCL1, CXCL 2 and CXCL 3; CCL 2, CCL 3, CCL 4 and CCL 8, using nomenclature outlined by Zlotnick and Yoshie, *Immunity*, 2000, 12:121-127. Chemokines have been found with an inflammatory model of pulmonary hypertension. (Kimura, Lab Invest 1998 78:571-81; Ikeda, Am J Physiol Heart Circ Physiol, 2002, 283(5):H2021-8). Unlike the in-vivo PVO model, which causes primarily obstructed blood flow, the model in the latter study incites inflammation and remodeling, which over weeks leads to vascular occlusion. Likewise, investigators have also found increased chemokine expression in lungs subjected to hilar ligation or clamping, which interrupts both perfusion and ventilation. The latter model differs significantly from in-vivo PVO because alveolar ventilation continues with in-vivo PVO. Thus the ischemic insult differs with in-vivo PVO versus hilar ligation.

Attempts have been made to analyze exhaled breath, including breath condensate, or otherwise measure certain components of exhaled breath. For example, U.S. Pat. Nos. 6,419,634 and 6,033,368 to Gaston IV et al. disclose a disposable device with a coolant coaxially surrounding a tube in order to cool exhaled breath sufficiently to cause condensation on the walls of the inner tube. Unfortunately, the device is designed for the measurement of nitrogen oxides and is not intended to facilitate protein or eicosinoid determinations on breath condensate. As a result, it suffers from a number of drawbacks. First, the Gaston device is mounted directly on the analyzer, and thus is too large and too cumbersome to use at the bedside for collection of small volumes of condensate in emergency department or other ambulatory patients. The Gaston device also suffers from inefficient sample collection inasmuch as the sample must be aggregated in one chamber and then transferred by the combined actions of droplet accretion and gravity to a separate second chamber for analysis. Perhaps worse, the Gaston device is incapable of use separate from the analyzer, in that the apparatus collects condensate in a chamber specifically designed for spectrophotometric analysis for nitrogen oxides, and thus has no port or other accessible reservoir from which condensate may be aspirated, aliquotted or otherwise withdrawn and subsequently transferred to a separate assay well to measure the components of the panel described above.

Further, although Gaston mentions the use of a device similar to a syringe plunger in expressing condensed fluid down its inner tube, Gaston fails to solve the problem of how to integrate such a plunger with the inlet tube. Also, even the inclusion of a plunger to express fluid down the inner tube of the Gaston device would still fail to solve the additional problem described previously; that is, Gaston still discloses no simple way to remove the fluid for removing and transferring the collected fluid for testing outside of the analyzing chamber. Finally, the Gaston coolant is not calibrated to permit condensation of a calibrated amount of condensate from a limited number of breaths. Instead, the Gaston device requires a lengthy period of sustained breathing in order to collect a sufficient quantity of condensate, a problem that is exacerbated by the absence of a plunger to more efficiently remove condensate from the device. This is due in large part to the considerable quantities of condensate that are necessary in Gaston for the intended type of testing to be performed thereon. As discussed previously, a major purpose of the present application is to collect relatively the small quantities of condensate necessary to perform the types of tests described above. Because such testing was not anticipated by Gaston, the Gaston device was not developed to permit such testing. Thus, a need exists for a fast and convenient apparatus and method for collecting small amounts of breath condensate in a manner that permits aliquotting as desired for the performance of tests such as the ones described above.

SUMMARY OF THE PRESENT INVENTION

It is hypothesized that the ability to measure particular biomarkers in exhaled breath water vapor, such as the ones described above, can assist in determining the presence and severity of lung ischemia. Lung ischemia can be caused by multiple processes, including thromboembolism, sickle cell disease, fat and air embolism. The ability to collect breath condensate rapidly and easily with a point-of-care device would improve the clinical utility of breath-based diagnosis for this purpose, particularly in the emergency department or clinic setting. The devices described herein are designed to allow a patient to breath into a handheld disposable chamber to facilitate the collection of approximately 100-1000 microliters of aerosolized and vaporized water and solutes, which can then be analyzed for the presence of specific proteins and other organic compounds, using enzyme-linked immunoassay, and the measurement of the proportion of carbon monoxide relative to nitric oxide using laser spectrophotometry.

It is an object of the present invention to provide a method of allowing cold-trapping of exhaled water vapor in a portable device.

It is another object of the present invention to provide a mechanism to permit use of frozen water of a known volume such that the ice melts after a known number of exhalations to permit collection of condensed exhaled water aerosol and vapor.

It is yet another object of the present invention to provide a breath condensate collection device having a series of valves to prevent contamination by water vapor and ambient air.

It is still another object of the present invention to provide a breath condensate collection device using a plunger-type mechanism to express collected condensate into a small reservoir to facilitate fluid collection.

It is yet another object of the present invention to construct a breath condensate collection device using materials to allow minimal cost of the device such that it is a disposable unit to minimize cost of the device.

It is still another object of the present invention to provide a method for the collection and aliquotting of a breath condensate sample in an expeditious fashion to facilitate testing for vasoconstrictor molecules, the measurement of the CO-to-NO ratio and the measurement of chemokine proteins.

The present invention comprises apparatuses and methods for non-invasively collecting breath condensate from a patient for testing purposes. Broadly defined, the present invention according to one aspect is a breath condensate collection apparatus, including: a central chamber having double side walls and first and second opposing ends, where the double side walls include an inner side wall and an outer side wall in spaced relationship to one another; a coolant material sealed between the inner and outer side walls for cooling at least the inner walls of the central chamber; a breath input assembly disposed on the outside of the outer side wall of the central chamber and penetrating both the inner and outer side walls such that the interior of the breath input assembly is in fluid communication with the interior of the central chamber; a plunger assembly having a piston and a handle, the piston being slidably disposed in the interior of the central chamber in snug contact with the inner side wall and the handle extending from the first end of the central chamber so as to permit the piston to be moved within the central chamber; and a breath condensate collection port, disposed at the second end of the central chamber, in fluid communication with the interior of the central chamber.

In features of this aspect, the plunger assembly is adjustable between a fully retracted position and a fully depressed position, and when the plunger is in its fully retracted position, the fluid connection between the breath input assembly and the central chamber lies in between the piston and the second end of the central chamber; the location of the breath input assembly on the outside of the outer side wall of the central chamber is adjacent the first end of the central chamber; the central chamber includes an end wall at the second end thereof, and the breath condensate collection port is disposed in the end wall of the central chamber; the piston includes a surface facing toward the second end of the central chamber, a protrusion is disposed on the surface of the piston, and the protrusion is adapted to fit into the breath condensate collection port when the plunger assembly is fully depressed into the central chamber; the breath condensate collection port and the protrusion are each semi-conical in shape; one or more grooves are disposed in the sides of the protrusion to facilitate guiding breath condensate toward the breath condensate collection port; one or more internal passages are disposed in the interior of the protrusion to facilitate guiding breath condensate toward the breath condensate collection port; the breath condensate collection port is disposed on the outside of the outer side wall of the central chamber adjacent the second end thereof; the breath condensate collection port is disposed on the bottom of the central chamber, and the breath condensate collection apparatus also includes an outlet and an outlet valve disposed on the top of the outer side wall of the central chamber adjacent the second end thereof; the breath condensate collection apparatus also includes a cap for temporarily sealing the breath condensate collection port; the breath condensate collection apparatus defines a main axis, the breath input assembly has a mouthpiece and a tube structure connecting the mouthpiece to the side of the central chamber, and the mouthpiece is generally oriented in parallel to the main axis of the breath condensate collection apparatus; and the breath condensate collection apparatus also includes at least one clip, mounted at the first end of the central chamber, for locking the handle of the plunger assembly in a fully depressed position to facilitate transport or handling of the breath condensate collection apparatus until breath condensate collected therein may be removed.

The present invention, according to another aspect of the present invention, is a method of collecting breath condensate, including: providing a central chamber having double side walls, first and second opposing ends, a coolant material sealed between the inner and outer side walls for cooling at least the inner walls of the central chamber, and a breath condensate collection port disposed at the second end of the central chamber; lowering the temperature of the coolant material to chill at least the inner walls of the central chamber; receiving, in the interior of the central chamber, exhaled breath from a patient, delivered through the inner and outer side walls via a breath input assembly disposed on the outside of the outer side wall of the central chamber; condensing portions of the exhaled breath on the inner surfaces of the inner walls of the central chamber; expressing condensate, produced during the condensing step, from the central chamber by depressing a plunger assembly through the central chamber, thereby forcing the condensate into the breath condensate collection port; and aspirating the expressed condensate from the breath condensate collection port for analysis thereof.

In features of this aspect, the aspirating step includes aspirating the expressed condensate into a pipette, and the method also includes transferring the condensate from the pipette to a separate assay well for analysis thereof; the providing step includes providing a central chamber having an outlet and outlet valve disposed on the top of the outer side wall of the central chamber adjacent the second end thereof and having the breath condensate collection port disposed on the bottom of the central chamber, and the method also includes temporarily sealing the breath condensate collection port during the receiving and condensing steps; and the step of providing includes providing a central chamber having at least one clip mounted at the first end of the central chamber, and the method also includes, after expressing the condensate by depressing the plunger assembly, a step of locking, via the at least one clip, the handle of the plunger assembly in a fully depressed position to facilitate transport or handling of the breath condensate collection apparatus until aspirating the expressed condensate.

The present invention, according to another aspect of the present invention, is a breath condensate collection apparatus, including: a central chamber having double side walls including an inner side wall and an outer side wall in spaced relationship to one another; a coolant material sealed between the inner and outer side walls for cooling at least the inner walls of the central chamber; a breath input assembly, the interior of which is in fluid communication with the interior of the central chamber; one or more obstructive structures arranged in the interior of the central chamber for increasing the surface area on which condensate may form; and a breath condensate collection port in fluid communication with the interior of the central chamber.

In features of this aspect, the obstructive structures include grid-like structures; the obstructive structures include discrete geometric structures; the discrete geometric structures include spherical objects; the discrete geometric structures are formed from metal; the discrete geometric structures are formed from glass; the obstructive structures are fixed in place within the interior of the central chamber; the obstructive structures are free-floating within the interior of the central chamber; and movement of the obstructive structures is restricted to a particular portion of the central chamber.

The present invention, according to another aspect of the present invention, is a method of collecting breath condensate, including: providing a double-walled central chamber having one or more obstructive structures arranged in the interior thereof and a coolant material sealed between the inner and outer side walls for cooling at least the inner walls of the central chamber; lowering the temperature of the coolant material to chill at least the inner walls of the central chamber and the obstructive structures; receiving, in the interior of the central chamber, exhaled breath from a patient; condensing portions of the exhaled breath on the inner surfaces of the inner walls of the central chamber and on the obstructive structures; and removing condensate, produced during the condensing step, from the central chamber.

In features of this aspect, the removing step includes washing the condensate from the obstructive structures; the washing step includes adding an amount of liquid to the central chamber, and the amount is selected to correspond to the amount of condensate present in the central chamber; the washing step includes adding an amount of liquid to the central chamber, and the amount is selected to correspond to the amount of condensate likely to be present in the central chamber after the patient exhales into the central chamber for a predetermined period of time; the washing step includes adding an amount of liquid to the central chamber, and the amount is selected to correspond to the amount of condensate likely to be present in the central chamber after the patient completes a predetermined number of exhalations into the central chamber; and the method further includes removing the obstructive structures from the central chamber before carrying out the washing step.

The present invention, according to another aspect of the present invention, is a method of collecting breath condensate, including: providing a double-walled central chamber having a removable outlet assembly and a coolant material sealed between the inner and outer side walls for cooling at least the inner walls of the central chamber; lowering the temperature of the coolant material to chill at least the inner walls of the central chamber; receiving, in the interior of the central chamber, exhaled breath from a patient; condensing portions of the exhaled breath on the inner surfaces of the inner walls of the central chamber; removing the outlet assembly and replacing it with a sampling well; and moving condensate, produced during the condensing step, from the central chamber to the sampling well.

In features of this aspect, the step of moving condensate includes washing condensate from the central chamber into the sampling well with a known liquid; the step of washing condensate includes introducing a predetermined quantity of the known liquid into the central chamber, mixing the predetermined quantity of the known liquid with the condensate, and draining the known liquid and the condensate from the central chamber into the sampling well; the step of removing the outlet assembly includes creating an opening into the central chamber, and the step of introducing includes introducing the known liquid through the opening; the method further includes storing the known liquid in the sampling well before replacing the outlet assembly with the sampling well; and the known liquid is a buffer solution.

The present invention, according to another aspect of the present invention, is a method of collecting breath condensate, including: providing a double-walled central chamber having one or more obstructive structures arranged in the interior thereof and a coolant material sealed between the inner and outer side walls for cooling at least the inner walls of the central chamber; calibrating the walls and coolant material of the double-walled central chamber such that, when beginning at a predetermined temperature, a chosen number of breaths, received from a typical patient, creates a sufficient amount of breath condensate to be collected on the inner surfaces of the inner walls of the central chamber; lowering the temperature of the coolant material to the predetermined temperature to chill at least the inner walls of the central chamber; receiving, in the interior of the central chamber, a plurality of exhalations from a particular patient, where the number of exhalations is within a predetermined range established on the basis of the chosen number of breaths; condensing portions of the exhalations, received from the patient, on the inner surfaces of the inner walls of the central chamber; and removing condensate, produced during the condensing step, from the central chamber.

In features of this aspect, the predetermined range is 10 to 25 breaths, inclusive; the predetermined temperature is the temperature of a standard freezer; and the predetermined temperature is 0° F.

BRIEF DESCRIPTION OF THE DRAWINGS

Further features, embodiments, and advantages of the present invention will become apparent from the following detailed description with reference to the drawings, wherein.

DETAILED DESCRIPTION OF THE PREFERRED EMBODIMENTS

Referring now to the drawings, in which like numerals represent like components throughout the several views, a variety of breath condensate collection apparatuses 10, 110, 210, 310, in accordance with the preferred embodiments of the present invention, is next shown and described.

Figure 1:
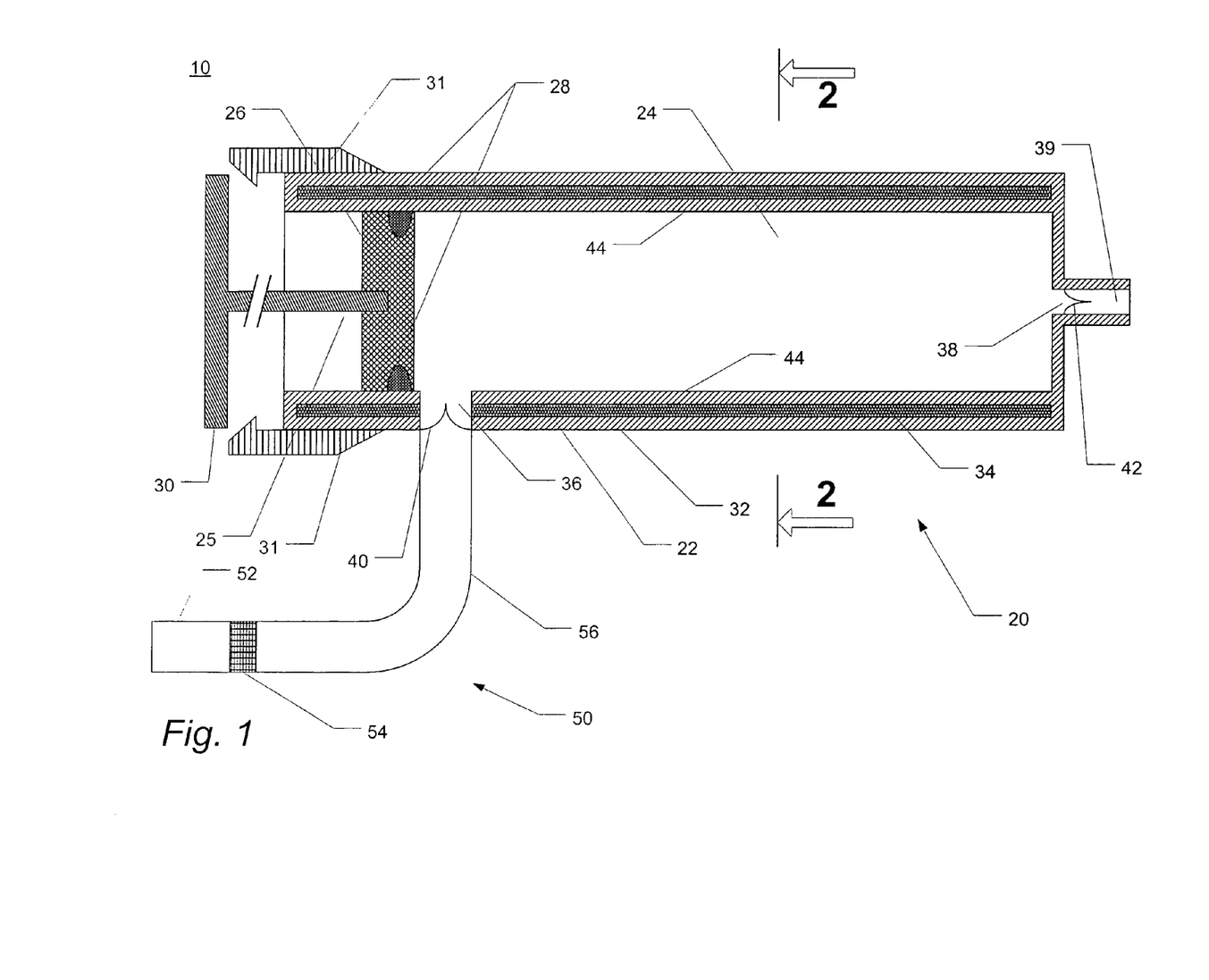
FIG. 1 is a side cross-sectional schematic view of a breath condensate collection apparatus in accordance with a first preferred embodiment of the present invention.
Figure 2:
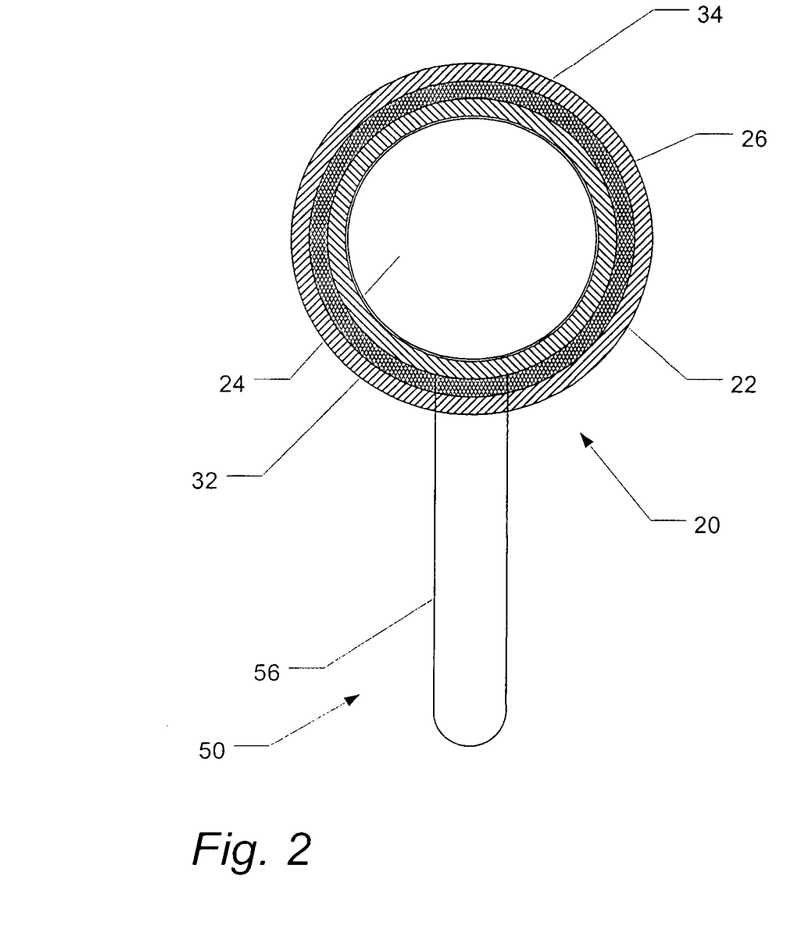
FIG. 2 is a right end cross-sectional view of the apparatus of FIG. 1, taken along line 2-2, showing the double-wall construction.
Figure 3:
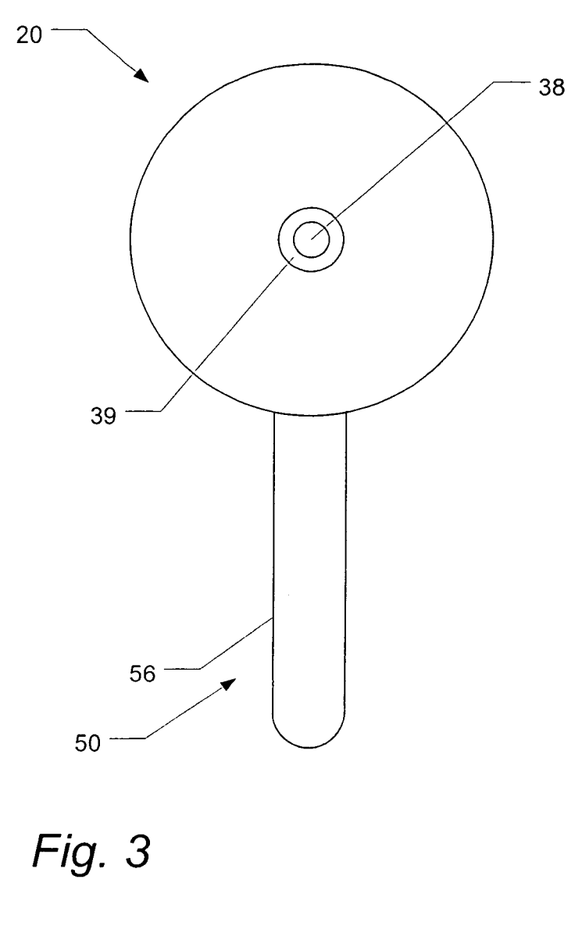
FIG. 3 is a right end view of the apparatus of FIG. 1.

FIG. 1 is a side cross-sectional schematic view of a breath condensate collection apparatus 10 in accordance with a preferred embodiment of the present invention. The breath condensate collection apparatus 10 includes a double-walled syringe 20 and a breath input assembly 50. The inner wall 22 of the syringe 20 defines a central cylinder 24 in which is fitted a plunger assembly 25 that includes a piston 26, a rubber gasket 28 and a handle 30 extending from one end of the syringe 20. The outer wall 32 is arranged around the inner wall 22 in such a way as to create a narrow space between the inner and outer walls 22, 32. FIG. 2 is a right end cross-sectional view of the apparatus 10 of FIG. 1, taken along line 2-2, showing the double-wall construction, and FIG. 3 is a right end view of the apparatus 10 of FIG. 1. During manufacture, the space between the inner and outer walls 22, 32 may be filled with a jacket of coolant material 34, and the outer wall 32 may then be sealed to the inner wall 22 to prevent leakage. In a preferred embodiment, water may be used as the coolant material 34, but it should be clear that other materials may likewise be used, such as polyethylene glycol ("PEG") and the like.

The syringe 20 further includes an inlet 36, an outlet 38, a collection port 39 and a pair of one-way valves 40, 42. The first valve 40 is an intake valve that may be disposed in or adjacent to the inlet 36, while the second valve 42 is an exit valve that may be disposed in or adjacent to the outlet 38 in order to facilitate the passage of exhaled air through the central cylinder 24 in only a single direction. The outlet valve 42 is preferably disposed between the central cylinder 24 and the collection port 39 for purposes that will be made evident hereinbelow. The outlet 38 is preferably disposed at the end opposite the plunger handle 30 in order to permit materials collected within the central cylinder 24 to be expressed through the outlet 38 by the piston 26. The valves 40, 42 are illustrated only schematically in the various drawings, but they may, for example, include two or three self-sealing leaves formed from plastic or another deformable polymer. The design of such valves would be apparent to those of ordinary skill in the art.

Further, because the piston 26 fills one end of the syringe 20 and the outlet 38 is disposed in the opposite end, the inlet 36 is preferably arranged to penetrate both the inner and outer walls 22, 32 on the side of the syringe 20. In order to cause the most interaction between exhaled air passing through the central cylinder 24 and the inner surfaces 44 of the inner wall 22, the inlet 36 is preferably disposed as close to the piston 26 as possible; however, it will be clear that other arrangements of these components are likewise possible without departing from the scope of the present invention.

The breath input assembly 50 includes a mouthpiece 52, a filter 54 and any tubing 56 necessary to guide exhaled breath from the mouthpiece 52 to the inlet 36 of the syringe 20. The mouthpiece 52 is of suitable size and shape so as to permit comfortable contact with the mouth area of a patient. The filter 54, which may comprise a polymer material having perforations or successive intrusions therein, may be arranged within the tubing 56 between the mouthpiece 52 and the syringe inlet 36 to prevent saliva and other liquid or solid matter of a minimum size from passing therethrough and into the syringe 20. Saliva may be further prevented from reaching the central cylinder 24 by arranging the breath input assembly 50 beneath the syringe 20, so that air passing through the breath input assembly 50 moves upward. In this arrangement, the effect of gravity on the saliva and other liquid or solid matter helps to prevent such matter from passing up into the central chamber 24, as it instead tends to collect in the tubing 56.

The tubing 56 is preferably configured so as to avoid interference between the mouthpiece 52, or any other part of the tubing 56, and the operation of the plunger assembly 25, as such operation is described herein. More preferably, the mouthpiece 52 is oriented to be generally parallel with the syringe 20 and the plunger assembly 25 therein, or in other words, the mouthpiece 52 is oriented in parallel to the main axis defined by the syringe 20. In this orientation, exhaled breath may be received from a patient without causing interference to the operation of the plunger assembly 25, and condensate formed on the inside of the syringe 20 as the patient uses the apparatus 10 will tend to drain downward toward the outlet 38.

The dimensions of the apparatus 10 are chosen so that a sufficient volume of condensate may be collected in a relatively short period of time using an apparatus 10 that is small and light enough to be easily held by a patient or attendant and that does not require the patient to change his breathing patterns. The walls 22, 32 and other structures of the apparatus 10 are preferably constructed of a material that tends not to bind to proteins, such as platinum-cured silicon, but other suitable materials may include, but are not limited to, glass, plastic, polyethylene, polycarbonate, or polyvinyl or other synthetic polymer. The plunger assembly 25 may is likewise preferably constructed from a non-protein-binding material, but may be constructed from any suitable inert material including, but not limited to, plastic, vinyl, polyethylene, rubber, platinum-cured silicon or TEFLON®. In a preferred embodiment, the syringe 20 is between 10 and 20 cm long with a diameter of between 2 and 5 cm, and the collection port 39 is between 5 and 20 mm long with an internal diameter of between 3 and 10 mm. The thickness of the coolant jacket 34 may be between 1 and 10 mm, and the sample volume, expressed from a single use, is preferably between 100 μL and 1000 μL, although it may be possible to obtain useful results from samples as small as 25 μL.

In operation, one or more syringes 20 are first stored in a refrigeration device, such as a conventional household or commercial freezer, that is capable of lowering the temperature to approximately 0° F., thus freezing the jacket of coolant material 34 contained between the inner and outer walls 22, 32 of the syringe 20. When a patient is to be examined, a single syringe 20 is first withdrawn from the freezer. If the breath input assembly 50 or mouthpiece 52 is stored separately from the rest of the apparatus 10, then the apparatus 10 is assembled for use by coupling the various components together. Next, the patient positions the mouthpiece 52 in a sealed relationship to his mouth area and exhales into the mouthpiece 52. The exhaled breath is guided through the tubing 56 and into the central cylinder 24 via the inlet 36. The intake valve 40 is forced open by positive pressure, but in the absence of such pressure it prevents air within the central cylinder 24 from escaping through the inlet 36. The exhaled breath then exits through the outlet 38 on the end of the cylinder 24 opposite the intake end. The exit valve 42 permits air to pass out of the central cylinder 24 only when positive pressure exists on the cylinder side of the valve 42, while in the absence of such pressure the valve 42 prevents ambient air from entering the central cylinder 24 via the outlet 38.

As the patient exhales through the apparatus 10, the moisture in the exhaled breath begins to condense on the inner surfaces 44 of the central cylinder 24. Because of the depressed temperature of the coolant 34 and the syringe 20, the condensate may freeze immediately on the inner surface 44. The collection port 39 is preferably nipple-shaped and approximately 1 cm long with a diameter small enough to cause some minimal resistance to the exhalation of the patient. The diameter is preferably chosen so as to slow the rate of expiration such that each exhalation requires approximately 5 seconds to complete. This increases the amount of time for exhaled breath to equilibrate with the inside surfaces 44 of the central cylinder 24.

Figure 4:
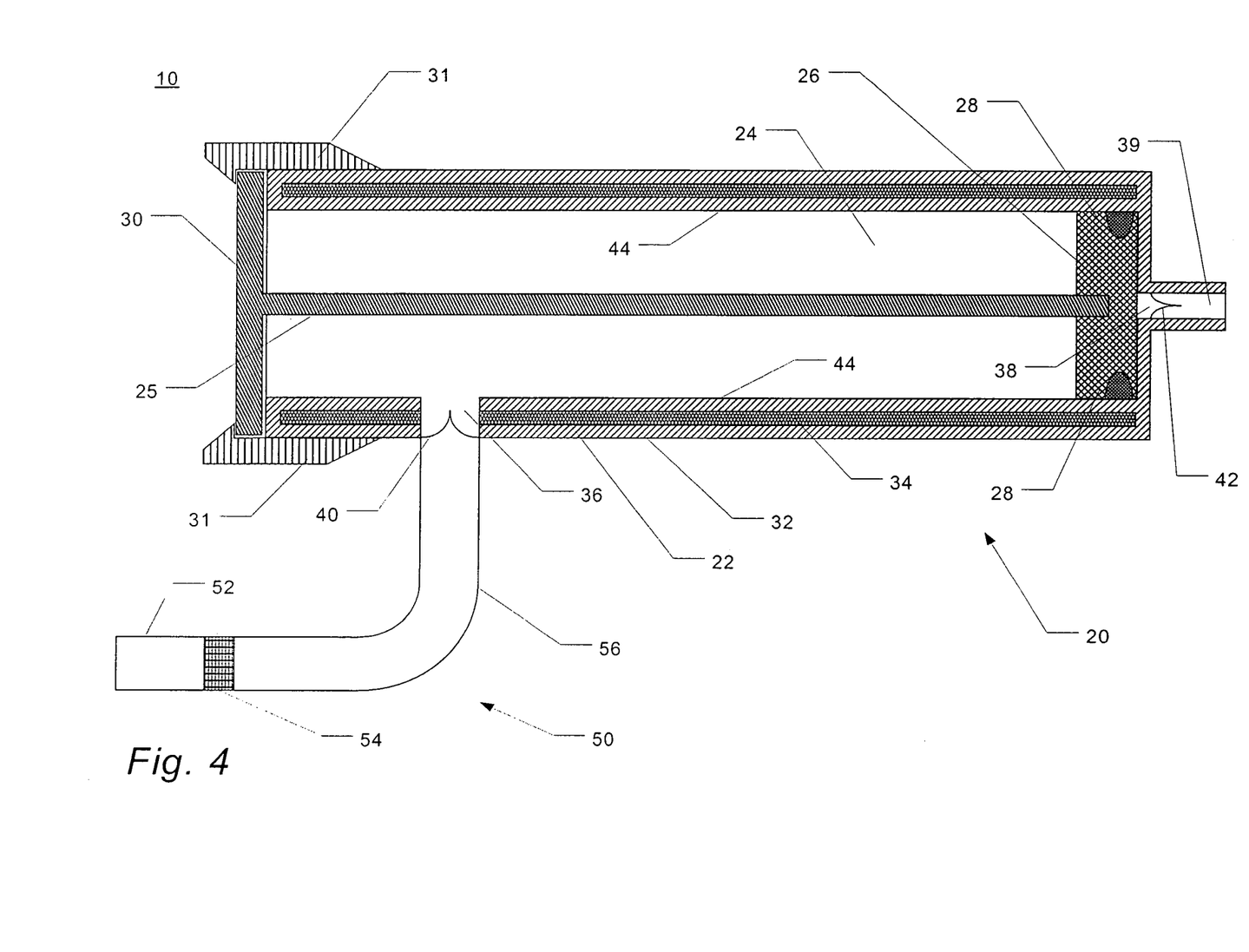
FIG. 4 is a side cross-sectional schematic view of the breath condensate collection apparatus of FIG. 1 with the plunger assembly in a fully depressed position.

As the patient continues to exhale through the apparatus 10, the frozen coolant 34 begins to melt. The composition, volume and thickness of the coolant jacket 34 surrounding the internal cylinder 24 is preferably calibrated such that the coolant 34 begins to melt after approximately 10-15 exhalations by the patient. Once the material 34 melts or thaws after the desired number of exhalations, the condensate likewise can begin to melt. Once the condensate is melted, the plunger assembly 25 may be depressed to express the collected condensate sample through the outlet 38 and into the collection port 39. FIG. 4 is a side cross-sectional schematic view of the breath condensate collection apparatus 10 of FIG. 1 with the plunger assembly 25 in a fully depressed position. The location of the exit valve 42 in the outlet 38 between the central cylinder 24 and the collection port 39 then permits the collected condensate to be aspirated from the collection port 39 using a conventional pipette (not shown). The condensate may then be transferred from the pipette to a separate assay well for analysis thereof as desired. Finally, once the condensate has been collected and withdrawn from the collection port 39, the entire apparatus 10 may be disposed of according to conventional waste disposition procedures.

Although not required, the plunger assembly 25 of the breath condensate collection apparatus 10 may further include one or more clips 31 disposed around the end of the syringe 20 opposite the collection port 39. These clips 31 are preferably formed from a resilient material and are designed to be deformed away from the syringe 20 as the plunger handle 30 is forced therebetween. The clips 31 are then biased back into place by their natural resiliency once the handle 30 is completely depressed into the syringe 20 as shown in FIG. 4. Once in this position, the plunger assembly 25 is effectively and conveniently locked in place by the clips 31, thereby permitting the syringe 20 to be transported and handled much more safely and reliably. It should be apparent, however, that such clips 31 are not necessary in order to be able to practice the various embodiments of the present invention.

Figure 5:
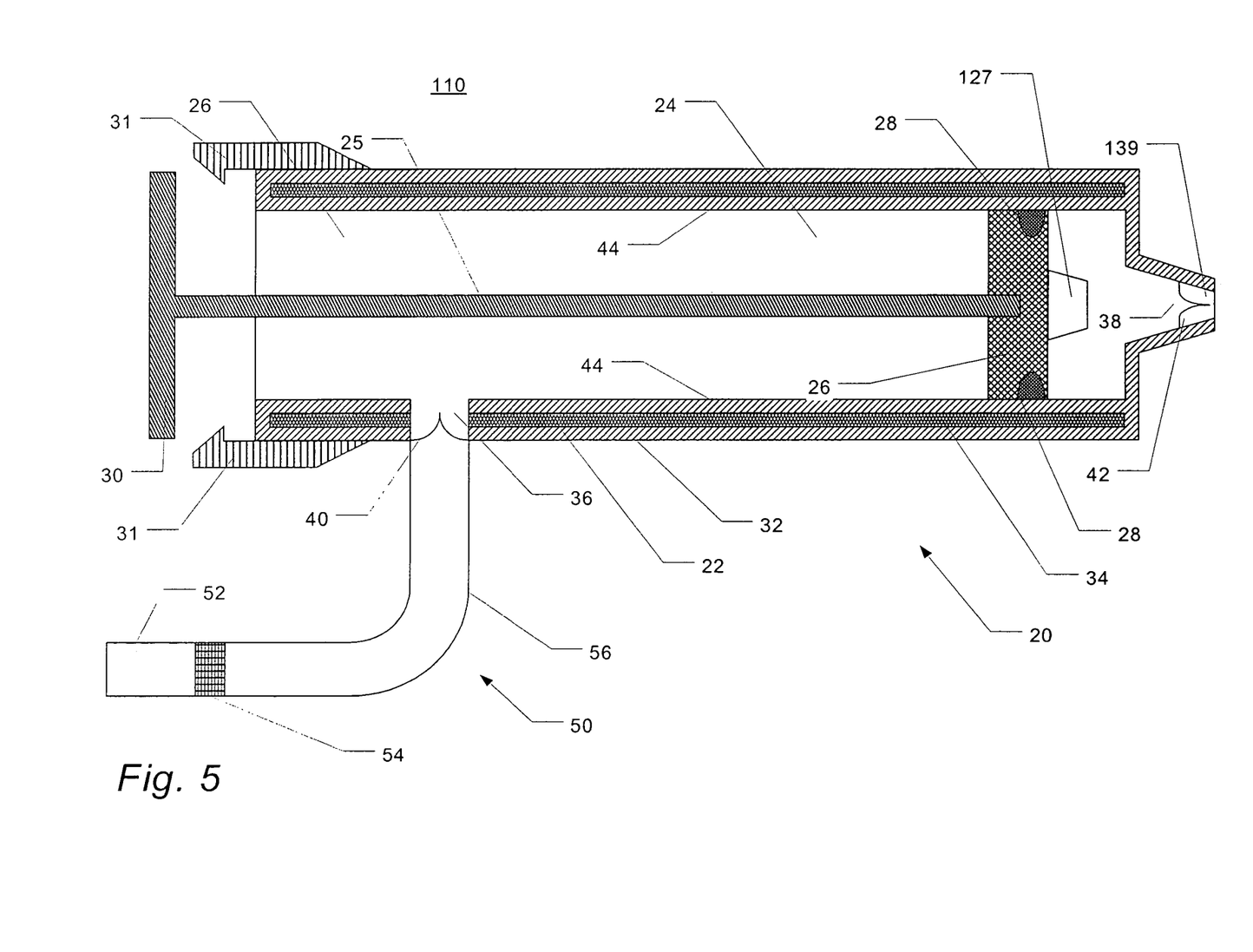
FIG. 5 is a side cross-sectional schematic view of a breath condensate collection apparatus in accordance with a second preferred embodiment of the present invention.

FIG. 5 is a side cross-sectional schematic view of a breath condensate collection apparatus 110 in accordance with a second preferred embodiment of the present invention. This apparatus 110 may be identical to the apparatus 10 of the first preferred embodiment, except that a semi-conical protrusion 127 (shown schematically in FIG. 5) is disposed on the surface of the piston 26 facing the outlet 38, the collection port 139 is sized and shaped to matingly receive the protrusion 127 therein, and the exit valve 42 is located at the distal end of the collection port 139. The collection port 139 may then be connected to a calorimetric device designed to detect condensate analytes.

Notably, although the exit valve 42 and protrusion 127 are shown only schematically in the drawings, the exit valve 42 is preferably positioned as close to the end of the collection port 139 as possible, and the protrusion 127 is preferably sized and shaped so as to abut the valve 42 when the plunger assembly 25 is fully depressed into the central cylinder 24. This design minimizes the amount of fluid that will remain in the syringe 20 when the plunger assembly 25 is fully depressed, and thus minimizes the amount of condensate that is available for subsequent testing.

Figure 6A:
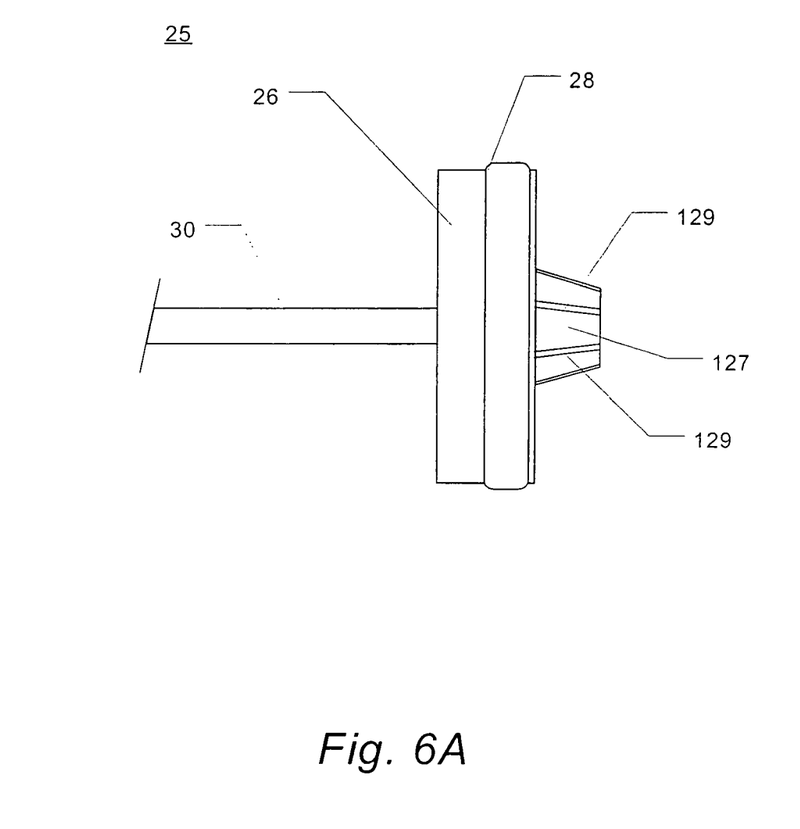
FIG. 6A is a partial side view of the plunger assembly of FIG. 5, illustrating one type of protrusion.
Figure 6B:
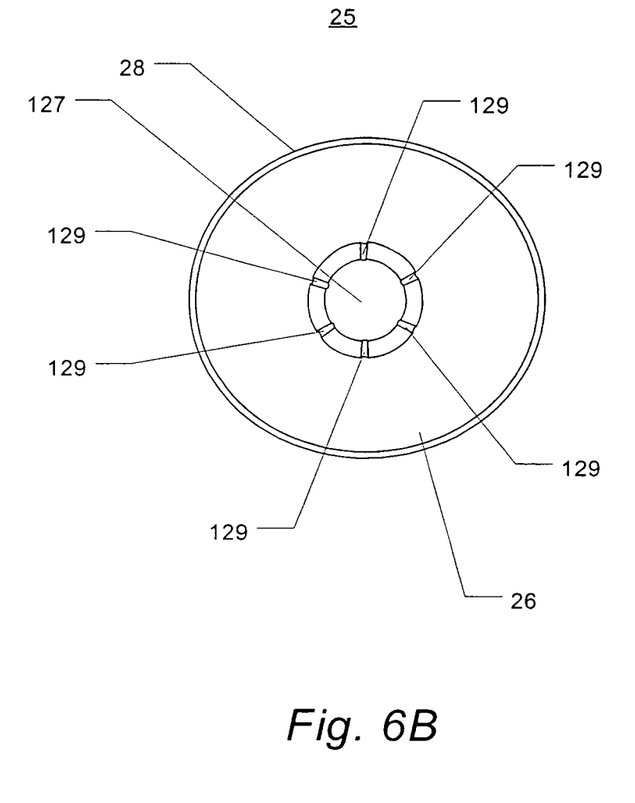
FIG. 6B is a right end view of the plunger assembly of FIG. 6A.

FIGS. 6A and 6B are a partial side view and a right end view, respectively, of the plunger assembly 25 of FIG. 5, illustrating one type of protrusion 127. This type of protrusion 127 includes a series of grooves 129 arranged in the surface thereof and extending from the base of the protrusion 127 to the tip. As the piston 26 is pushed into the very end of the central cylinder 24, the grooves 129 serve as conduits for the condensate remaining in the syringe 20, thus permitting a small amount of additional condensate to be collected via the collection port 139 rather than be trapped in the end of the central cylinder 24. This effect could be further enhanced by the inclusion of additional groove structures (not shown) in the flat surface of the piston 26 that could be used to guide condensate to the grooves 129 in the protrusion 127.

Figure 7A:
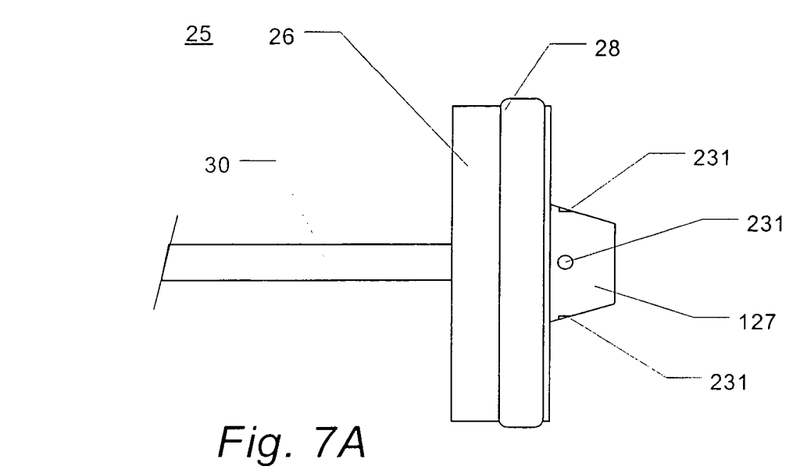
FIG. 7A is a partial side view of the plunger assembly of FIG. 5, illustrating another type of protrusion.
Figure 7B:
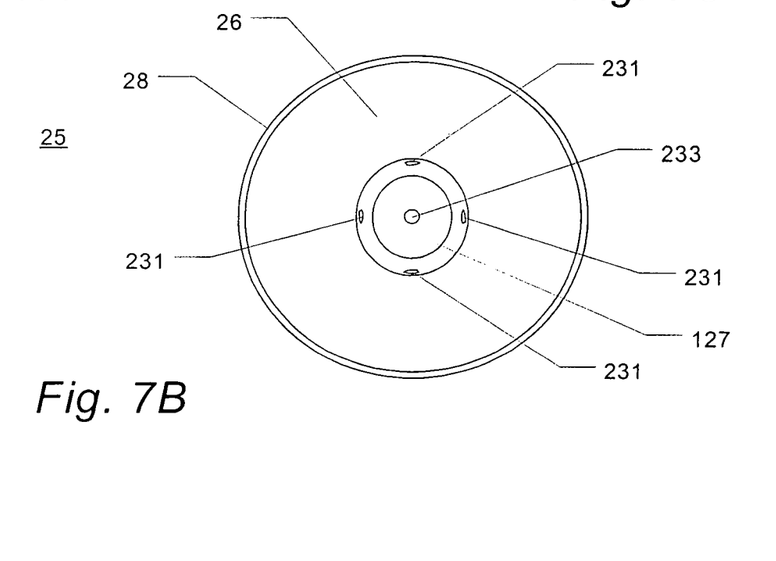
FIG. 7B is a right end view of the plunger assembly of FIG. 7A.
Figure 7C:
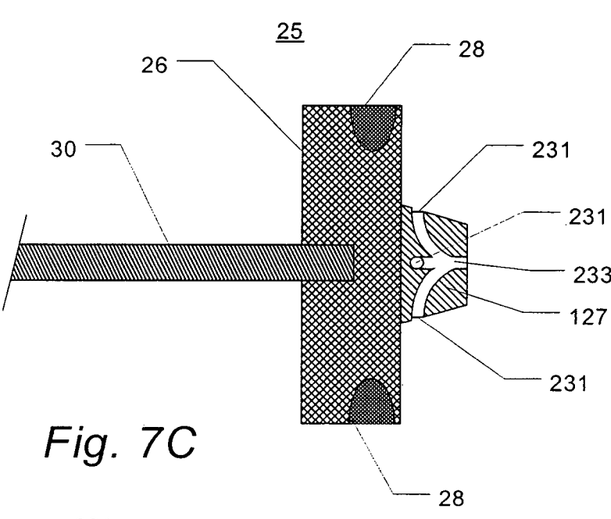
FIG. 7C is a partial side cross-sectional view of the plunger assembly of FIG. 7A.

FIGS. 7A, 7B and 7C are a partial side view, a right end view and a partial side cross-sectional view, respectively, of the plunger assembly 25 of FIG. 5, illustrating another type of protrusion 127. This type of protrusion 127 includes a plurality of openings 231 arranged around the base of the protrusion 127 and connecting to a hollow shaft 233 that exits through the tip of the protrusion 127. The openings 231 and central shaft 233 may be between 1 and 2 mm in diameter. Once again, as the piston 26 is pushed into the very end of the central cylinder 24, the openings 231 and hollow shaft 233 serve as conduits for the condensate remaining in the syringe 20, thus permitting a small amount of additional condensate to be collected via the collection port 139 rather than be trapped in the end of the central cylinder 24. This effect could also be further enhanced by the inclusion of additional groove structures (not shown) in the flat surface of the piston 26 that could be used to guide condensate to the openings 231 in the protrusion 127. The central shaft 233 could also be fitted with a rigid but hollow tube structure (not shown) of between 1 and 2 mm (external diameter) to provide a needle-like extension through which the fluid sample could be directed and extruded when the plunger assembly 25 is fully depressed.

Figure 8:
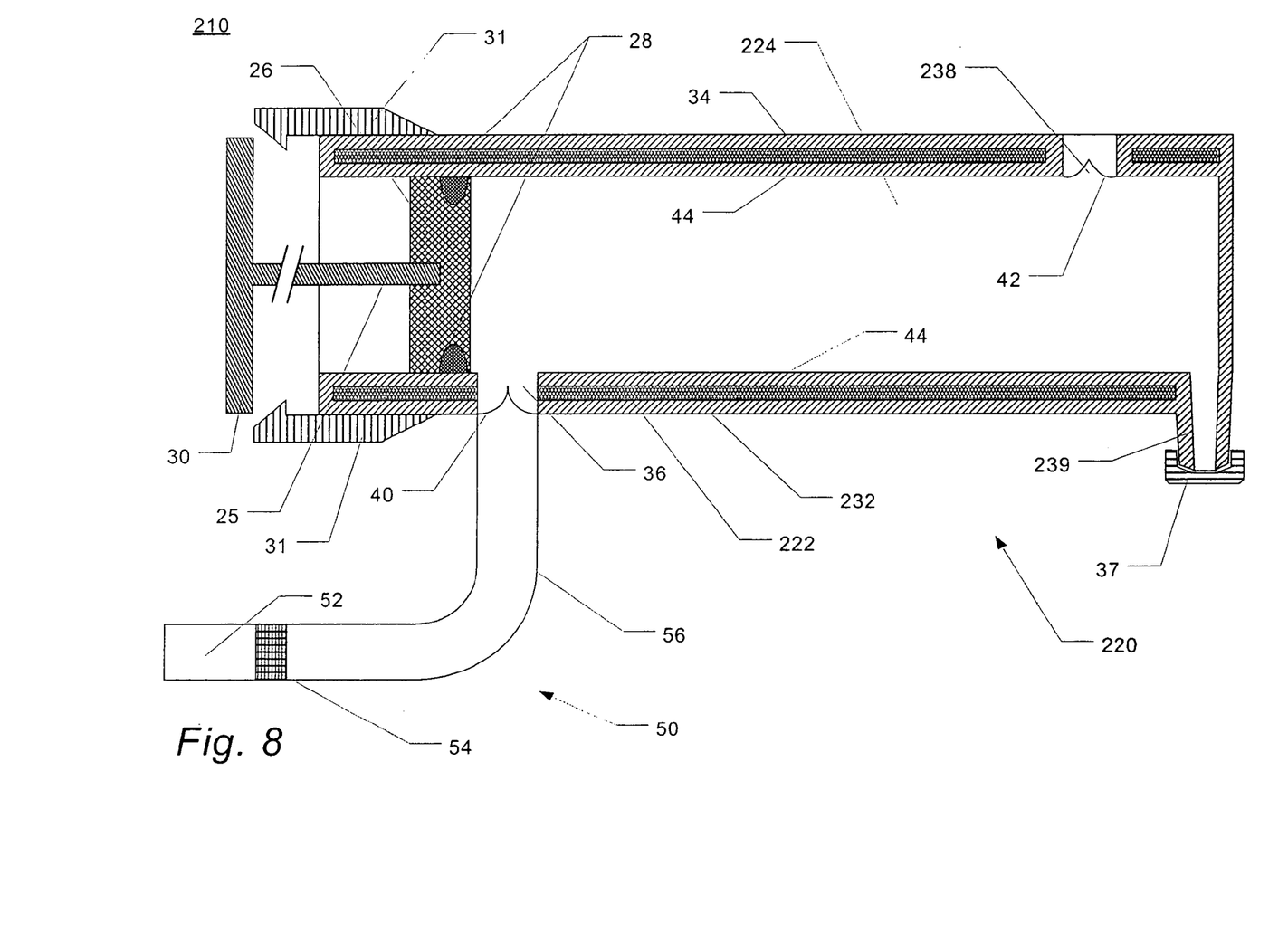
FIG. 8 is a side cross-sectional schematic view of a breath condensate collection apparatus in accordance with a third preferred embodiment of the present invention.

FIG. 8 is a side cross-sectional schematic view of a breath condensate collection apparatus 210 in accordance with a third preferred embodiment of the present invention. Like the apparatuses of the first and second embodiments 10, 110, this breath condensate collection apparatus 210 includes a syringe 220, having inner and outer walls 222, 232, and a breath input assembly 50. The syringe 220 and the breath input assembly 50 are generally similar to those of the first embodiment. However, unlike the first embodiment, the outlet 238 and the outlet valve 42 are disposed on the top of the syringe 220, near the end opposite the plunger handle 30, and the syringe 220 further includes a collection port 239, disposed on the bottom of the syringe 220 at the very end of the central cylinder 224, and a cap 37 for covering the collection port 239. The cap may be threaded or otherwise adapted for secure connection of the cap 37 to the collection port 239 in order to temporarily close the collection port 239. This apparatus 210 functions the same way as the first apparatus embodiment 10 except that exhaled breath exits through the outlet 238 on the top of the syringe 220, but condensate may be collected and expressed from the central cylinder 224 via the collection port 239 on the bottom of the syringe 220. The cap 37 prevents exhaled air from passing through the collection port 239, but may be unscrewed or otherwise removed when it is desired to collection the condensate from the central cylinder 224. This may be particularly useful, for example, in expressing condensate directly into an analyzer temporarily or permanently mounted on or adjacent the syringe 220, as described in co-pending and commonly-assigned U.S. Provisional Patent Application No. 60/447,581, filed Feb. 14, 2003.

Figure 9:
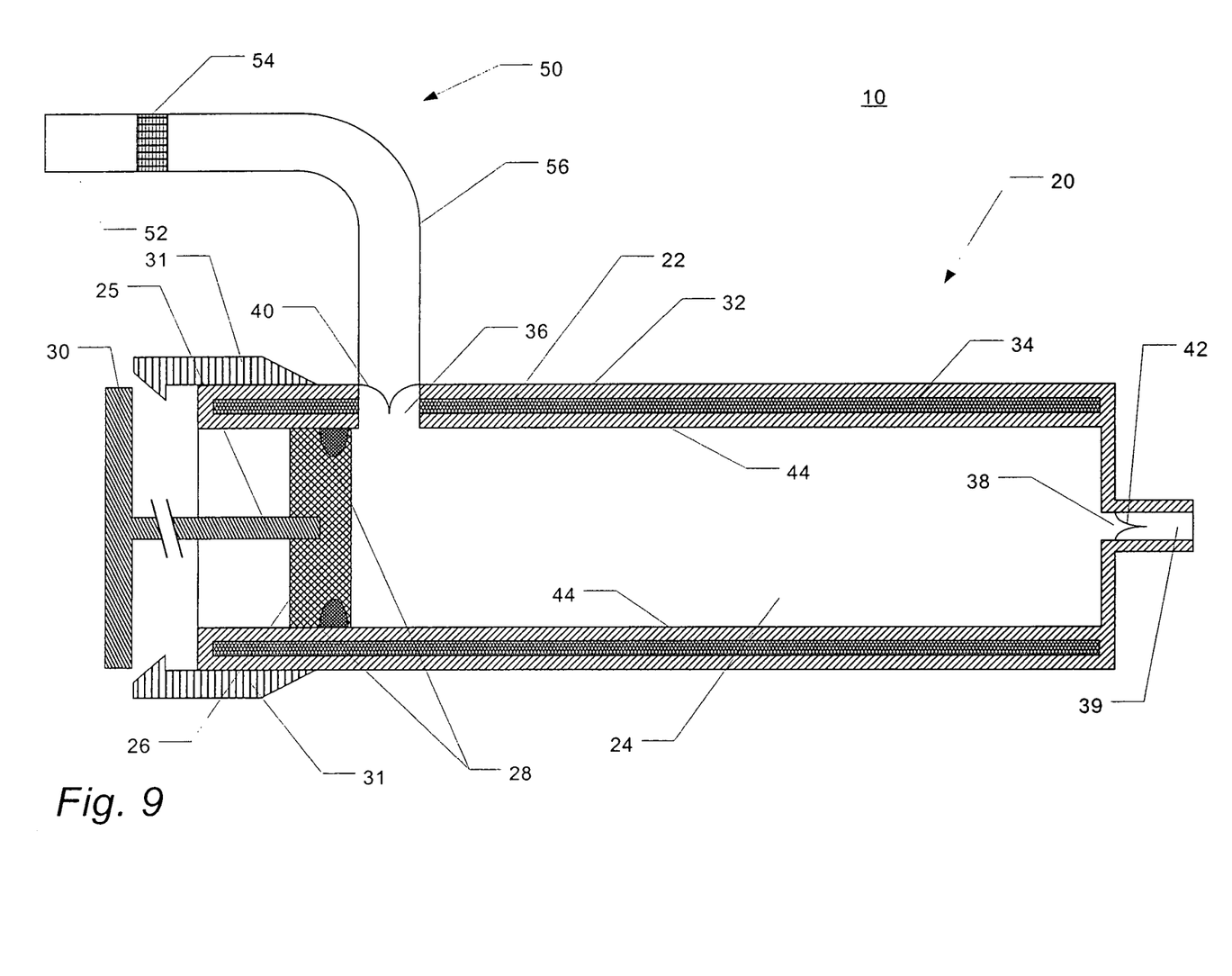
FIG. 9 is a side cross-sectional schematic view of the breath condensate collection apparatus of FIG. 1, shown in an inverted orientation.

As described previously, it is advantageous for the breath input assembly 50 in each of the three embodiments 10, 110, 210 discussed thus far to be arranged beneath the respective syringe 20, 220 in order to aid in preventing saliva and other matter from reaching the central cylinder or chamber 24, 224. However, it will be apparent that the breath input assembly 50 may instead be oriented such that the breath input assembly 50 is located at the top of the syringe 20, 220. FIG. 9 is a side cross-sectional schematic view of the breath condensate collection apparatus 10 of FIG. 1, shown in an inverted orientation, whereby the breath input assembly 50 is disposed at the top of the syringe 20. Although saliva may be more likely to enter the syringe 20, it should be apparent that other features of the present invention may not be affected by this arrangement. Although not shown, the apparatuses 110, 210 of the second and third embodiments may likewise be rearranged, although it should be noted that the breath input assembly 50 in the third apparatus 210 would have to be placed on the opposite side of the collection port 239 in order to facilitate proper operation thereof.

Figure 10:
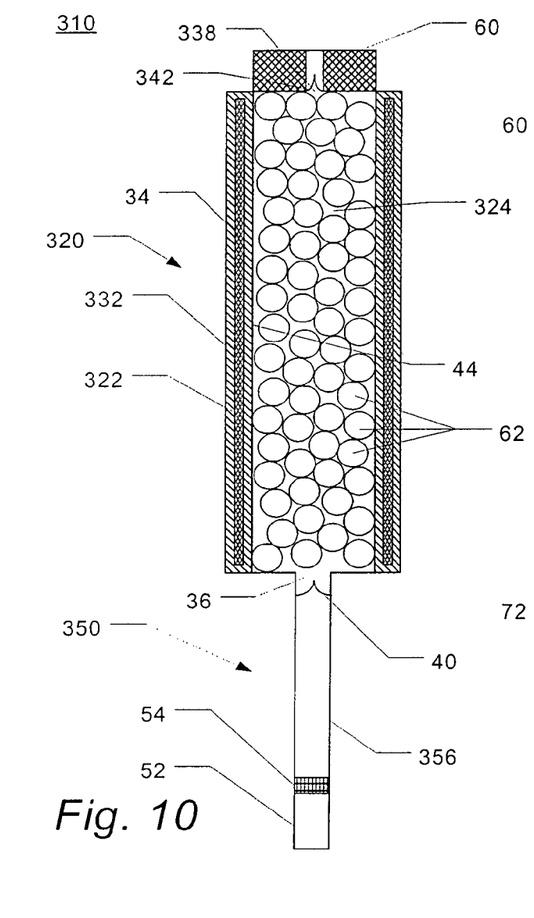
FIG. 10 is a side cross-sectional schematic view of a breath condensate collection apparatus in accordance with a fourth preferred embodiment of the present invention.

FIG. 10 is a side cross-sectional schematic view of a breath condensate collection apparatus 310 in accordance with a fourth preferred embodiment of the present invention. Like the apparatus 10 of the first embodiment, this breath condensate collection apparatus 310 includes a double-walled syringe 320 and a breath input assembly 350. The inner wall 322 of the syringe 320 defines a central chamber 324, but unlike the central cylinder 24 of the first embodiment, the central chamber 324 of the alternative embodiment need not be cylindrical. The outer wall 332 is arranged around the inner wall 322 in such a way as to create a narrow space between the inner and outer walls 322, 332. Like the apparatus 10 of the first embodiment, however, the space between the inner and outer walls 322, 332 may be filled during manufacture with a jacket of coolant material 34, and the outer wall 332 is then sealed to the inner wall 322 to prevent leakage.

Figures 11, 12, 13:
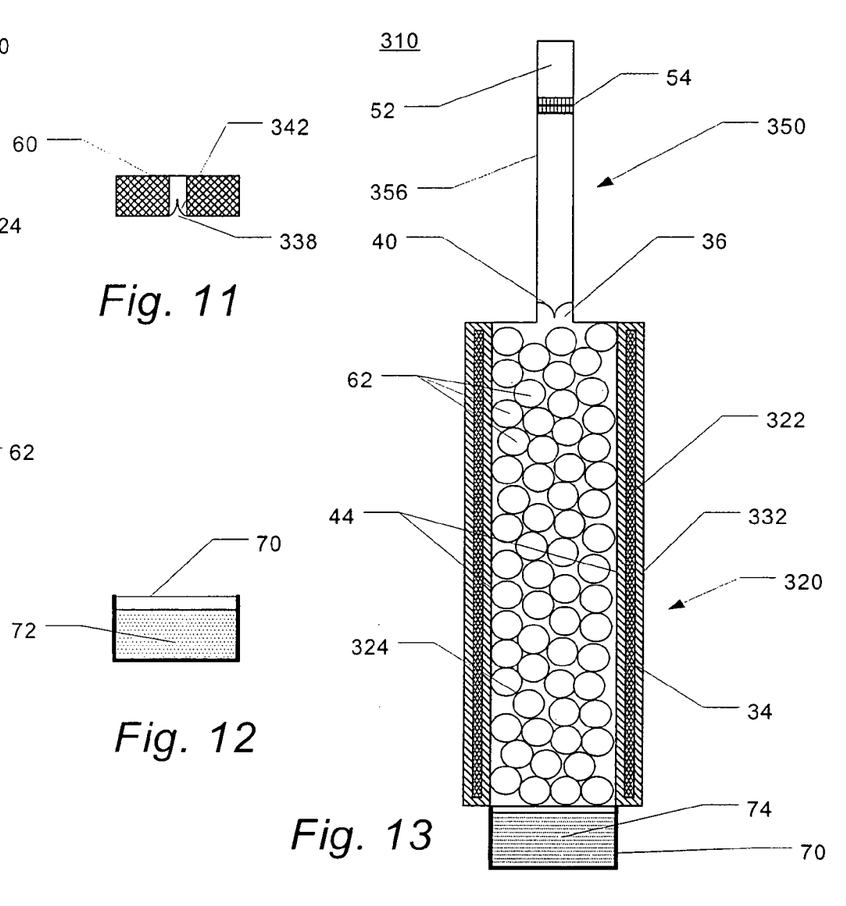
FIG. 11 is a cross-sectional schematic view of a removable outlet cap for use with the apparatus of FIG. 10.
FIG. 12 is a cross-sectional schematic view of a removable sampling well for use with the apparatus of FIG. 10.
FIG. 13 is a side cross-sectional schematic view of the breath condensate collection apparatus of FIG. 10 with the sampling well installed thereon.

The syringe 320 further includes an inlet 36, an outlet cap 60 and a first one-way valve 40. The first valve 40 is an intake valve that may be disposed in or adjacent to the inlet 36. FIG. 11 is a cross-sectional schematic view of a removable outlet cap 60 for use with the apparatus of FIG. 10. The outlet cap 60 includes an outlet 338 and a second valve 342, which is an exit valve disposed in or adjacent to the outlet 338 in order to facilitate the passage of exhaled air through the central chamber 324 in only a single direction. The outlet cap 60 is preferably disposed at the end of the central chamber 324 opposite the inlet 36.

The breath input assembly 350 includes a mouthpiece 52, a filter 54 and any tubing 356 necessary to guide exhaled breath from the mouthpiece 52 to the inlet 36 of the syringe 320. As with the first embodiment of the apparatus 10, the mouthpiece 52 is of suitable size and shape so as to permit comfortable contact with the mouth area of a patient, and the filter 54 may be arranged within the tubing 356 between the mouthpiece 52 and the syringe inlet 36 to prevent saliva and other liquid or solid matter of a minimum size from passing therethrough and into the syringe 320.

Unlike the embodiments described previously, the apparatus 310 of the fourth embodiment does not include a plunger assembly. Instead, as illustrated in FIG. 10, one or more obstructive internal structures 62 may be arranged inside the central chamber 324 in order to increase the surface area with which exhaled breath that passes through the central chamber 324 may come in contact. Suitable obstructive structures 62 may include grid-like structures and other baffles, spheres such as those shown in FIG. 10, or other geometric shapes formed from metal, glass, or other suitable materials. These structures 62 may be held in place within the syringe 320 using appropriate screens, bosses or the like (not shown). If cooled in like manner to the syringe 20 of the first embodiment, breath condensate may subsequently be produced inside the central chamber 324 more efficiently.

However, because the obstructive structures 62 occupy the interior of the central chamber 324, removal of the condensate collected thereon may require flushing the interior of the central chamber 324 with a suitable buffer solution 72 of known volume and composition. For example, the solution may consist of distilled water, or water containing an organic dye to indicate the pH of the solution using visual or spectrophotometric colorimetry. In a preferred method of operation of the alternative embodiment shown in FIG. 10, the apparatus 310 is oriented horizontally (not shown), and breath condensate is collected on the inner surfaces 44 of the central chamber 324 and on the obstructive structures 62 in the same manner as described with respect to the first embodiment. The apparatus 310 may then be rotated to the vertical orientation shown in FIG. 10. With the apparatus 310 in the illustrated orientation, the outlet cap 60 may be removed without danger of the condensate inside the syringe 320 escaping. Suitable connection means, such as corresponding screw threads or the like, are preferably provided on the syringe 320 and the outlet cap 60 to facilitate such removal.

Once the outlet cap 60 has been removed, the buffer solution 72 may be added to the central chamber 324 in order to wash the collected condensate therefrom. Suitable buffer solutions and volumes will be apparent to those of ordinary skill of the art. FIG. 12 is a cross-sectional schematic view of a removable sampling well 70 for use with the apparatus of FIG. 10. With the outlet cap 60 removed and the apparatus oriented as shown in FIG. 10, a sampling well 70 such as that shown in FIG. 12 may be fastened onto the open end of the syringe 320 to close that end. FIG. 13 is a side cross-sectional schematic view of the breath condensate collection apparatus 310 of FIG. 10 with the sampling well 70 installed thereon. Once the sampling well 70 is in place, the entire apparatus 310 may be inverted to the orientation shown in FIG. 13, thus causing the buffer solution 72 to wash the collected breath condensate out the bottom of the syringe 320 and into the sampling well 70. Once collected in the sampling well 70, the sampling well 70 may once again be removed and the buffered condensate 74 may be aliquotted for testing as desired.

In a variation of the various embodiments described herein, any of the syringes 10, 110, 210, 310 may alternatively be cooled via an endothermic reaction, such as that created when $NH_4NO_3$ is hydrated with water in a 1:4 molar ratio, to produce a temperature below 0° C. for approximately 10 minutes. This may be facilitated by storing water in the space between the walls of the syringe 10, 110, 210, 310 in breakable ampules, surrounded by dry $NH_4NO_3$, or by sealing only the $NH_4NO_3$ in the same space, to be hydrated or otherwise injected with water via a needle port. $NH_4NO_3$ may be prepared because the reaction may be triggered by injecting the $NH_4NO_3$ material with a preset volume of tap water or saline via the needle port, similar to the way a nurse would "flush" an IV line, but it should be apparent that other materials may likewise be used to create a suitable endothermic reaction. For example, a commercial gel refrigerant that may be activated by slight compression of the outer wall of the syringe may likewise be used. One such material is Cold Ice, produced by Cold Ice, Inc. of Oakland, Calif.

Once the sample is obtained using any of the various apparatuses 10, 110, 210, 310 described herein, or by some alternative means, a battery of tests may be performed on the sample in order to detect lung ischemia. The battery of tests may include measuring or testing for fibrinopeptides, thromboxane B2, platelet activating factor, leukotrienes C, D and E, carbon monoxide-to-nitric oxide ratio and chemokine and other proteins. Each of these has specific purposes, as described below. The various tests may all be performed in a manner well known to those of ordinary skill in the art.

Measurement of fibrinopeptides in breath condensate is believed to have the potential to allow more localized measurement of the presence of clot in the lung vasulature. As described previously, thrombin cleaves fibrinogen A peptide from fibrinogen as a prerequisite to fibrin gelation. Owing to its small size, it is hypothesized that fibrinopeptides will traverse the alveolar membrane, and equilibrate in alveolar fluid, and thus will be found in exhaled condensate. Thus, the presence of fibrinopeptides in the breath condensate sample would indicate the presence of clot.

Also, pulmonary vascular constriction may be detected by measuring $PGF_{2\alpha}$, thromboxane $B_2$, PAF, leukotrienes C, D, and E, and the ratio of CO:NO in condensate, thus providing a basis for initiating pulmonary vasodilator therapy or COX1,2 inhibition. Our laboratory has used an experimental pulmonary vascular occlusion (PVO), induced by venous infusion of polystyrene microspheres in a rat, to determine three major findings related to breath condensate analysis. We and others have found increased content of $PGF_{2\alpha}$, thromboxane $B_2$, platelet activating factor (PAF) and vasoconstrictive leukotrienes C, D, and E in the lung washings in our rat model. (Nakos, Am J Resp Crit Care Med 1998, 158:1504) The magnitude of the concentration of these vasoconstrictive agents correlated with the severity of hypoxemia and pulmonary hypertension. We also have found extremely elevated expression of the gene encoding heme oxygenase-1 but the nearly complete absence of expression of the gene encoding for the inducible enzyme, nitric oxide synthase. Heme oxygenase produces carbon monoxide (CO) from heme substrate whereas nitric oxide synthase produces nitric oxide (NO). Both are vasodilator substances. In rats subjected to PVO, we have also found early increases in lung gene expression of cytokine induced neutrophil attractant 1 and 2 (CINC 1 & 2), and monocyte/macrophage chemoattractant protein (MCP) 1 and 2, and monocyte/macrophage inflammatory proteins (MIP) 1 α and 1 β with concomitant increases in each protein in the washings from the lung airways and alveoli obtained as soon as 2 hours after induction of PE, and lasting up to 18 hours after PE induction. The chemoattractant molecules can cause the migration of leukocytes into the affected area, and through this mechanism, can potentiate injury during therapeutic reperfusion.

Further, the presence of certain chemokines in exhaled condensate is believed to predispose reperfusion injury. The chemokines discovered in rats included CINC 1, CINC 2, MIP 1α, MIP 1β, and MCP 1 and 2. The human homologues that will be tested in our device will include CXCL1, CXCL 2 and CXCL 3; CCL 2, CCL 3, CCL 4 and CCL 8, using nomenclature outlined by Zlotnick and Yoshie, *Immunity*, 2000; 12:121-127. Investigators have found chemokines with an inflammatory model of pulmonary hypertension. (Kimura, Lab Invest 1998 78:571-81; Ikeda, Am J Physiol Heart Circ Physiol, 2002, 283(5):H2021-8). Unlike the in-vivo PVO model, which causes primarily obstructed blood flow, the model in the latter study incites inflammation and remodeling, which over weeks leads to vascular occlusion. Likewise, investigators have also found increased chemokine expression in lungs subjected to hilar ligation or clamping, which interrupts both perfusion and ventilation. The latter model differs significantly from in-vivo PVO because alveolar ventilation continues with in-vivo PVO. Thus the ischemic insult differs with in-vivo PVO versus hilar ligation.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A method of collecting breath condensate using a breath condensate collection apparatus, the method comprising:

providing a central chamber having double side walls, first and second opposing ends, a coolant material sealed between the double side walls, consisting of an inner wall and an outer wall for cooling at least the inner wall of the central chamber, and a breath condensate collection port disposed at the second end of the central chamber;

lowering the temperature of the coolant material to chill at least the inner wall of the central chamber;

receiving, in an interior of the central chamber, exhaled breath from a patient, delivered through the double side walls via a breath input assembly disposed on the outside of the outer wall of the central chamber;

condensing portions of the exhaled breath on inner surfaces of the inner wall of the central chamber;

expressing condensate, produced during the condensing step, from the central chamber by depressing a plunger assembly through the central chamber, thereby forcing the condensate into the breath condensate collection port;

aspirating the expressed condensate from the breath condensate collection port for analysis thereof, wherein aspirating includes aspirating the expressed condensate into a pipette;

transferring the condensate from the pipette to a separate assay well for said analysis thereof; and temporarily sealing the breath condensate collection port during the receiving and condensing steps, wherein providing the central chamber includes providing a central chamber having an outlet and an outlet valve on top of the outer side wall of the central chamber adjacent the second end thereof and providing the breath condensate collection port on a bottom of the central chamber.

2. The method of claim 1, wherein providing the central chamber includes providing at least one clip mounted at the first end of the central chamber, the method further comprising:

after expressing the condensate by depressing the plunger assembly, locking, via the at least one clip, the handle of the plunger assembly in a fully depressed position to facilitate transport or handling of the breath condensate collection apparatus until said aspirating the expressed condensate.

3. The method of claim 1, wherein said breath input assembly is disposed underneath the central chamber.

* * * * *